United States Patent
Chen et al.

(10) Patent No.: US 9,290,799 B2
(45) Date of Patent: Mar. 22, 2016

(54) SYSTEM AND METHOD FOR DETECTING BIOLOGICAL MATERIALS

(71) Applicant: Industrial Technology Research Institute, Chutung, Hsinchu (TW)

(72) Inventors: Yi-Chang Chen, Taipei (TW); Jane SC Tsai, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/971,498

(22) Filed: Aug. 20, 2013

(65) Prior Publication Data

US 2014/0155278 A1 Jun. 5, 2014

Related U.S. Application Data

(60) Provisional application No. 61/691,541, filed on Aug. 21, 2012.

(51) Int. Cl.
*C12Q 1/68* (2006.01)
*C40B 20/04* (2006.01)
*G01N 33/543* (2006.01)

(52) U.S. Cl.
CPC .............. *C12Q 1/6837* (2013.01); *C12Q 1/682* (2013.01); *G01N 33/54333* (2013.01); *C12Q 1/6813* (2013.01); *C12Q 1/6827* (2013.01); *C12Q 2600/106* (2013.01); *C40B 20/04* (2013.01)

(58) Field of Classification Search
None
See application file for complete search history.

(56) References Cited

U.S. PATENT DOCUMENTS

| | | | |
|---|---|---|---|
| 6,403,309 B1 | 6/2002 | Iris | |
| 7,811,754 B2 | 10/2010 | Herron | |
| 8,017,327 B2 | 9/2011 | Wang | |
| 2002/0028457 A1* | 3/2002 | Empedocles et al. | 435/6 |
| 2006/0166239 A1* | 7/2006 | Chen et al. | 435/6 |
| 2007/0235692 A1 | 10/2007 | Wu | |
| 2007/0298426 A1 | 12/2007 | Chen | |
| 2009/0104789 A1 | 4/2009 | Mallick et al. | |
| 2012/0077195 A1 | 3/2012 | Li | |
| 2012/0141995 A1 | 6/2012 | Li | |
| 2012/0283109 A1* | 11/2012 | Liu | 506/4 |
| 2013/0005049 A1 | 1/2013 | Mao | |

FOREIGN PATENT DOCUMENTS

WO WO 2004071641 A2 * 8/2004
WO WO 2011038403 A1 * 3/2011

OTHER PUBLICATIONS

Templin et al., "Protein Microarrays and Multiplexed Sandwich Immunoassays: What Beats the Beads?" Comb. Chem. High Throughput Screen. 2004, 7:223-229.*
Wabuyele et al., "Approaching Real-Time Molecular Diagnostics: Single-Pair Fluorescence Resonance Energy Transfer (spFRET) Detection for the Analysis of Low Abundant Point Mutations in K-ras Oncogenes," J. Am. Chem. Soc. 2003, 125:6937-6945.*

(Continued)

*Primary Examiner* — Samuel Woolwine
*Assistant Examiner* — Kaijiang Zhang
(74) *Attorney, Agent, or Firm* — Cesari and McKenna, LLP

(57) ABSTRACT

A method of identifying a target biological material by using captures and probes. Each capture is specific for a kind of target. Each probe is designed to distinguish the type of the target. The captures and probes are each labeled with one or more detectable labels.

15 Claims, 5 Drawing Sheets

(56) References Cited

OTHER PUBLICATIONS

Yang et al., "PCR-free MDR1 polymorphism identification by gold nanoparticle probes," Anal. Bioanal. Chem. 2010, 397:1937-1945.*
Qiuying Huang, et al., Multicolor Combinatorial Probe Coding for Real-Time PCR, PLoS One, vol. 6, 2011.
Meni Wanunu, Nanopores: A journey towards DNA sequencing, Physics of Life Reviews 9 (2012) 125-158.
Karolyn Szuhai, et al., Nature Protocols, vol. 1 No. 1 2006.
Qiuying Huang, et al., Clinical Chemistry 53:10 1741-1748 (2007).
Cheng-Hsien Wu et al., Sequence-Specific Capture of Protein-DNA Complexes for Mass Spectrometric Protein Identification, PLoS One, vol. 6, No. 10, Oct. 2011.
Multiplex Immunoassay, http://www.bio-rad.com/evportal/de/AT/evolutionPortal.portal?_nfpb=true&_pageLabel=SolutionsLandingPage&catID=LUSM0E8UU, AWccessed Aug. 20, 2013, 3 Pages.
James H. Werner, et al., Progress towards single-molecule DNA sequencing: a one color demonstration, Journal of Biotchnology 102 (2003) 1-14.
Fu Xiong, et al. The Journal of Molecular Diagnostics, vol. 13, No. 4, Jul. 2011.
M.A. Augustin, Progress towards single-molecule sequencing: enzymatic synthesis of nucleotide-specifically labeled DNA, Journal of Biotechnology, 86 (2001) 289-301.
Jia Zhang, et al., On-off Regulation of 3' Exonuclease Excision to DNA Polymerization by Exo+ Polmerase, Journal of Biochemistry and Molecular Biology, vol. 36, No. 6, 2003.

* cited by examiner

SEQUENCE LISTING

<160> NUMBER OF SEQ ID NOS: 7

<210> SEQ ID NO 1
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 1
ctttggagac cagcccatgg ggacagagtc aga    33

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
gtcctcaatg ctcctcttcc c    21

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
gtcctcaatg ctcctcttcc c    21

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
cacatttggt ccattgtcat gtgt    24

<210> SEQ ID NO 5
<211> LENGTH: 23

```
<212> TYPE: DNA
<213> ORGANISM: Artificial sequence
<220> FEATURE:
<223> OTHER INFORMATION: Synthetic oligonucleotide

<400> SEQUENCE: 5
acatttggtc cattgtcatg tgc                                          23

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
cgggcttcct cttgaacacg                                              20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
cgggcttcct cttgaacaca                                              20
```

SYSTEM AND METHOD FOR DETECTING BIOLOGICAL MATERIALS

CROSS-REFERENCE TO RELATED APPLICATION

This application claims priority to U.S. Provisional Application No. 61/691,541, filed Aug. 21, 2012, the content of which is incorporated herein by reference in its entirety.

BACKGROUND

Diseases and conditions can be diagnosed by detecting the presence of diseased cells, pathogen genes, or mutated genes. For some diseases, detecting the presence of mutated genes can also be valuable for determining treatment and for prognosis. For example, detecting single nucleotide polymorphisms (SNPs) in the cytochrome P450 (CYP) gene and the vitamin K epoxide reductase 1 (VKOR1) gene can be used to select warfarin dosages for patients. In the practice of personalized medicine, the detection of clinically relevant mutations can be used to guide targeted therapeutic decisions.

Therefore, there is a need for methods and platforms for detection of nucleic acid molecules and other biological materials.

SUMMARY

Described herein is a method of identifying a biological material. The method includes:
providing a sample containing a biological material, wherein the biological material has a kind and a type;
adding to the sample one or more captures and one or more probes, each capture and each probe being labeled with one or more detectable labels, wherein each capture is specific for a kind of biological material and each probe is specific for a type of biological material, and the one or more captures are distinguishable from each other by their detectable labels and the one or more probes are distinguishable from each other by their detectable labels, whereby a combination of detectable labels identifies a kind and a type of the biological material;
allowing the one or more captures and the one or more probes to bind to the biological material; and
determining the detectable labels bound to the biological material, whereby the kind and the type of the biological material are identified.

Also described herein is a method of identifying one or more target nucleic acids. The method includes:
providing a sample containing nucleic acid molecules;
mixing the sample with one or more captures and one or more probes to obtain a mixture, wherein (i) each capture is labeled with one or more detectable labels such that it is distinguishable from the other captures by its detectable labels, and contains a capture nucleic acid sequence complementary to a first target sequence in a target nucleic acid, and (ii) each probe is labeled with one or more detectable labels such that it is distinguishable from the other probes by its detectable labels, and contains a probe sequence that is complementary to a second target sequence in a target nucleic acid, whereby a combination of detectable labels identifies a target nucleic acid molecule;
allowing the one or more captures and the one or more probes to hybridize to the nucleic acid molecules, thereby complexes each containing a target nucleic acid, a capture, and a probe are formed; and
determining the detectable labels bound to the complexes, whereby one or more target nucleic acids are identified.

The details of one or more embodiments are set forth in the accompanying drawing and the description below. Other features, objects, and advantages will be apparent from the description and drawing, and from the claims.

DETAILED DESCRIPTION

Figure 1:
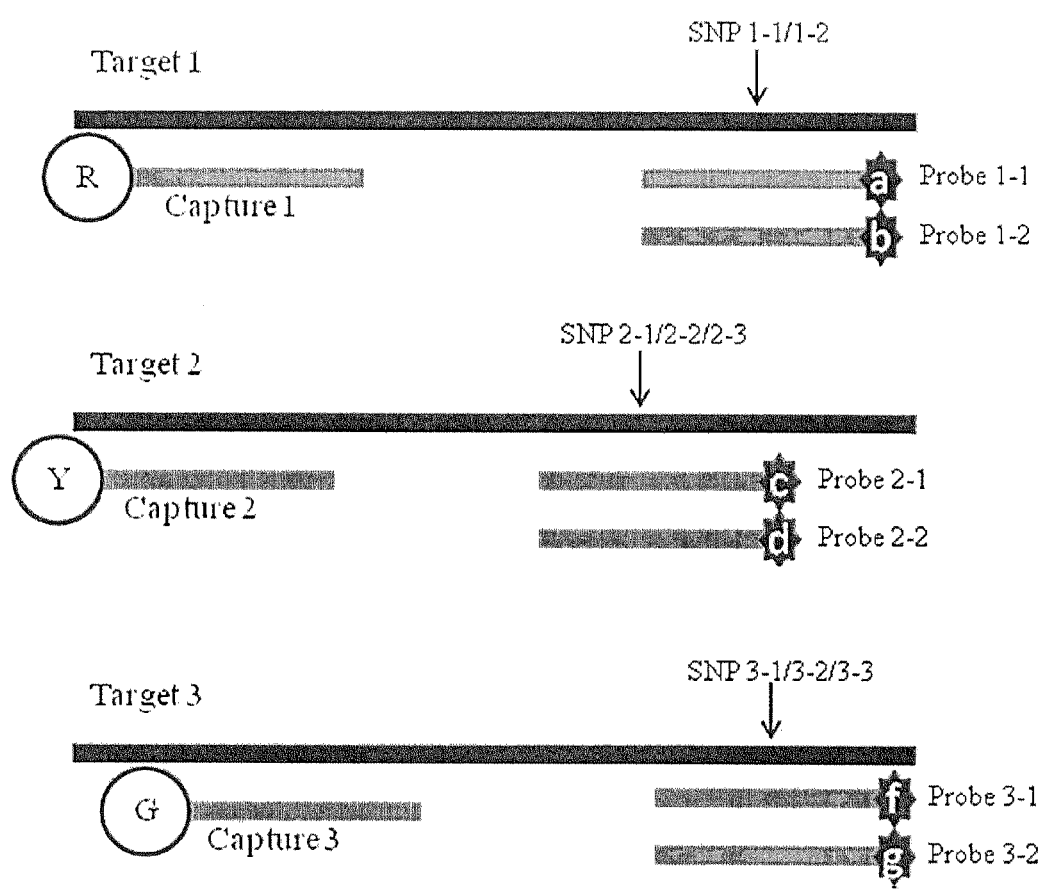
FIG. 1 is a schematic representation of exemplary nucleic acid captures and probes.

In the following detailed description, for purposes of explanation, numerous specific details are set forth in order to provide a thorough understanding of the disclosed embodiments. It will be apparent, however, that one or more embodiments may be practiced without these specific details.

Described herein is a method for the detection of biological materials. It can be used for analyzing the type, quantity, strength, or other physical, chemical, or biological characteristics of a sample. For example, the method can be utilized to determine organism species or genotypes. Applications of the method include molecular diagnostic tests.

General Methodology

The method utilizes captures and probes. Each capture is specific for a kind of target (e.g., a specific gene). Each probe is designed to further distinguish the target, e.g., to determine the type (e.g., genotype or a SNP) of the target.

The captures and probes each contain a binding moiety that binds to a biological material of interest, e.g., a nucleic acid, a polypeptide, a lipid, a glycolipid, a cell, a tissue, a pathogen, or an organism. Useful binding moieties include nucleic acids, antibodies, antibody fragments, antibody-like molecules (e.g., Affibody molecules, affilins, affitins, anticalins, and avimers), peptidomimetics, proteins, peptides, fusion proteins, receptors, ligands, DNA-protein hybrids, DNA-RNA hybrids, and RNA-protein hybrids. The method can be adapted to detect any biological materials by modifying the captures and probes such that they specifically recognize and bind the biological materials of interest.

The captures and probes are each labeled with one or more detectable labels, e.g., chromophores and fluorescent labels. The kind and the type of a target biological material are identified by a unique pre-defined code (e.g., a color code), which is the combination of the detectable labels associated with a specific capture and a specific probe.

Various detectable labels are known in the art. Examples of detectable labels include quantum dots, isotopic labels (e.g., radioactive or heavy isotopes), magnetic labels, spin labels, electric labels, thermal labels, colored labels (e.g., chromophores and fluorescent labels), luminescent labels (e.g., fluorescers and chemiluminescers), enzyme labels (e.g., horseradish peroxidase, alkaline phosphatase, luciferase, and β-galactosidase), antibody labels, and chemically modifiable labels (e.g., fluorescent labels, luminescent labels, bioluminescent labels, dyes, and enzymes). Detectable labels include those that can be visualized by any light sources, e.g., visible light, fluorescence, luminescence, LED, UV or laser, or a combination thereof. Examples of fluorescent labels include fluorescein, rhodamine, Lucifer Yellow, Texas Red, Alexa-Fluor dyes, Cy3, Cy5, Cy5.5, and Cy7.

If a set of captures includes a total of n different colors and a set of probes includes a total of m different colors, the set of captures and the set of probes together can be used to distinguish is $(2^n-1) \times (2^m-1)$ types of a biological material. Therefore, the methods described herein maximize the number of biological material kinds and the number of biological material types that can be distinguished using permutations and combinations of colors.

In one embodiment, to identify the kind and the type of a target biological material, a test sample suspected of containing a target of interest is mixed with a capture specific for that target (e.g., a specific gene) and one or more probes specific for one or more types of the target (e.g., a mutation or a SNP in the gene). Capture-probe-target complexes are identified by determining the detectable labels associated with the captures and probes used in the test. For example, capture-probe-target complexes can be subjected to imaging using a fluorescent microscope. Each detectable label can be visualized individually to obtain an image. The images thus obtained can then be digitally compiled and analyzed to identify the labels present and the intensities of the labels. A code (e.g., a color code) is thus determined, which indicates the kind and/or the type of the target. Positive and negative controls are typically included in a test. The strength of a signal obtained from the image analysis should be equal to or greater than that of the positive control to be considered as a positive signal.

Suitable imaging systems are commercially available. Image analysis can be carried out using methods or softwares known in the art, e.g., ImageJ.

The test sample used in the method can be from any source that contains or is suspected to contain the biological material of interest. For example, the sample can be obtained from a living organism (e.g., human, animal, plant, bacteria, fungi, protist, and virus), or an environmental source (e.g., water, air, or soil). The sample can be a bodily fluid such as plasma, serum, saliva, whole blood, semen, or urine, or a solid sample (e.g. a tissue sample, a cell pellet, a biopsy sample, and fecal matter). The biological material of interest can be first isolated or partially isolated from the sample. The biological material can also be enriched or concentrated, such as by using filtration or centrifugation.

The capture can include a small solid particle (e.g., a bead) to, for example, facilitate separation and identification of capture-probe-target complexes from unbound captures, probes, and targets. Any types of small solid particles, e.g., small synthetic particles or microspheres, that can be conjugated to a biological molecule are useful in the present method. Small solid particles composed of various materials (e.g., plastic, ceramic, glass, polystyrene, methylstyrene, an acrylic polymers, a paramagnetic material, carbon graphite, titanium dioxide, latex, Sepharose, agarose, cellulose, carboxymethyl cellulose, hydroxyethyl cellulose, a proteinaceous polymer, nylon, biotin, streptavidin, and Teflon) are known in the art or commercially available. Suitable particles can range from about 0.2 µm to about 200 µm (e.g., 1-3 µm) in diameter.

Methods of conjugating biological molecules (e.g., nucleic acid, proteins, and antibodies) to solid particles are known in the art. A biological molecule can be attached to a solid particle directly or indirectly via a linker.

Capture-probe-target complexes can be isolated or separated from samples using methods known in the art, e.g., washing and centrifugation. If biotin beads or streptavidin beads are used, streptavidin or biotin columns or immunoprecipitation can be used. If magnetic beads are used, magnetic devices can be used to isolate the complexes. A dielectrophoresis device can be used to separate magnetic beads of different sizes and materials. See, e.g., Medoro, G.; Manaresi, N.; Leonardi, A.; Altomare, L.; Tartagni, M.; Guerrieri, R. A Lab-on-a-Chip for Cell Detection and Manipulation. *IEEE Sensors Journal,* 2003, 3, 317-325; and U.S. Pat. No. 7,682,827.

The methods described herein can be used for a wide variety of purposes. For example, the methods can be used to diagnose genetic diseases (or a patient's or subject's risk therefore), to identify foreign sequences (e.g., viral sequences) incorporated into a target gene, or to test for infectious diseases, infectious organisms, or pathogens.

The term "subject" refers to an animal, or a human, and includes, but is not limited to, mammals, e.g., primates, pigs, rodents such as mice and rats, rabbits, guinea pigs, hamsters, cows, horses, cats, dogs, sheep, and goats.

The methods can be carried out on-site or in an off-site facility. The data, images, and results obtained using the methods can be uploaded, analyzed, and visualized on a hand-held device, e.g., a smart phone, a mobile device, or a tablet computer.

Nucleic Acid Tests

Described herein is a method for detecting nucleic acids, e.g., DNA, RNA, mRNA, and cDNA. For example, the method can be used to detect the presence of a genetic marker, an allele, a mutation, a SNP, or an another identifying genetic feature.

In a nucleic acid test, a capture can include a capture nucleic acid molecule, e.g., a single-stranded nucleic acid, that has a capture sequence (e.g., 30 to 100, or 30 to 60 nucleotides), which can specifically hybridize to a first target sequence within a target nucleic acid (e.g., a gene). The first target sequence does not contain any SNP or mutation of interest. In other words, a capture is designed to "capture," e.g., bind, a specific target nucleic acid, but not to detect any particular genetic features in that target. A capture is labeled with one or more detectable labels, e.g., a colored label. In a test to simultaneously detect multiple target nucleic acids or to determine whether one of a number targets is present in a sample, multiple captures each specific for a target nucleic acid can be employed. In such a test, each different capture is labeled with a different detectable label or combination of detectable labels, such that each capture is distinguishable from the others by its detectable label or labels A probe can contain a nucleic acid molecule having a probe sequence (e.g., 30 to 100, or to 60 nucleotides) that can specifically hybridize to a second target sequence in a target nucleic acid. The second target sequence includes one or more identifying features of interest, e.g., a SNP, a mutation, a genetic marker for a disorder, a sequence for identifying organism type or species, or any genetic alteration. A probe is also labeled with one or more detectable labels. In a test designed to detect multiple genetic alterations or features or to determine whether one of a number of features is present, different probes each specific for a genetic feature and labeled with a different detectable label or combination of detectable labels can be employed.

For example, as shown in FIG. 1, multiple captures and probes are designed to simultaneously detect SNPs (positions indicated by arrows) in three different target genes. Each of Capture 1, Capture 2, and Capture 3 is conjugated to a different colored bead (i.e., R, Y, or G-colored bead), and has a nucleic acid with a sequence that is complementary to a portion of Target 1, Target 2, or Target 3, respectively. For each target, probes each having a sequence that is complementary to a portion that contains a specific SNP (e.g., SNP 1-1 or 2-1) are generated. Each different probe is labeled with a different fluorescent label (e.g., a, b, c, or d). Therefore, each SNP is represented by a specific pre-determined color code, e.g., Ra, or Yc.

A skilled practitioner would appreciate that the above example is merely illustrative, and would be able to design captures and probes for different applications. Depending on the design of a test, different probes can share some detectable labels, as long as the different targets can be distinguished. For example, one probe can be labeled with fluorescent labels a and b, while another probe can be labeled with fluorescent labels a and c.

Figure 2:
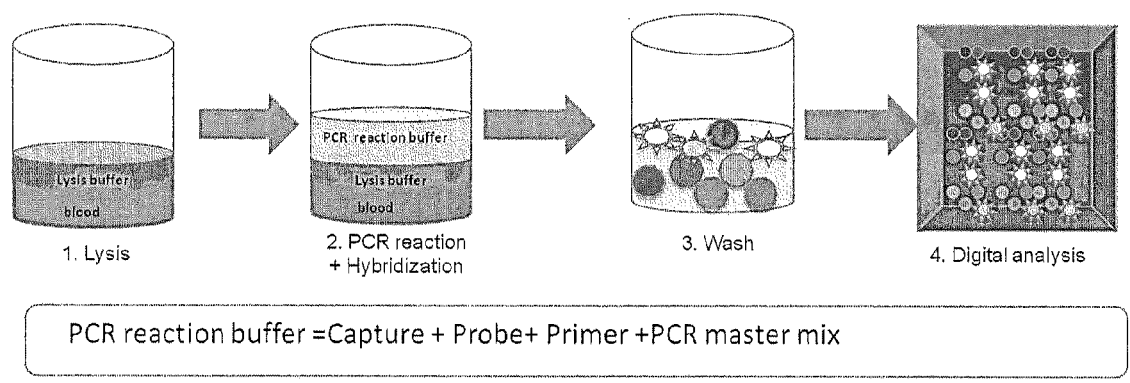
FIG. 2 is a schematic representation of an exemplary nucleic acid test.

An overview of an exemplary nucleic acid test is shown in FIG. 2. In step 1, in a tube, a blood sample is mixed with a lysis buffer (e.g., the lysis buffer described in Example 2 below) to release cellular contents. In step 2, captures, probes, primers for amplifying target nucleic acids, and PCR reagents are added to the same tube. PCR is then carried out in the same tube. Upon completion of the PCR reaction, the captures, the probes, and the amplified target nucleic acids are allowed to hybridize in the same tube. In step 3, the tube is washed. Capture-probe-target complexes remain in the tube. In step 4, a sample from the tube is subjected to image analysis.

As described above, the sample treatment step, the PCR step, the hybridization step, and the washing step can be carried out in a single container, e.g., a tube or a well of a microtiter plate.

A skilled person would be able to design appropriate capture and probe sequences based on the desired targets. A capture sequence and a probe sequence can each be complementary to their respective target sequences. Under appropriate conditions, there can be a certain degree of mismatch between a capture sequence or a probe sequence and its target sequence Hybridization reaction is carried out under appropriately stringent conditions. Such stringent conditions are well known in the art, and will vary predictably depending on the specific sequences of the targets, captures, and probes.

Nucleic acid tests can be carried out using emulsions, i.e., use of water-in-oil droplets. Microemulsions can be generated in which the aqueous compartments contain target nucleic acids, captures, probes, and other components. PCR, hybridization, or other reactions can then be carried out with the emulsions. In other words, each droplet in the emulsion is a microreactor. Methods of making microemulsions are known in the art. See, e.g., Williams et al., Nature Methods, 3(7):545-550 (2006), and Dressman et al., PNAS, 100(15) 8817-8822 (2003).

For example, an oil-surfactant mixture (containing, e.g., Span 80, Tween 80, Triton X-100, mineral oil, and a dye) and an aqueous phase (containing, e.g., a sample, buffers, water, DNA templates, primers, DNA polymerase, PCR reagents, captures, and probes) can be prepared. The concentrations of the DNA templates, probes and captures can be controlled to produce droplets that on average each contains a desired number of molecules, e.g., a single template DNA molecule to allow clonal expansion of that single template in a droplet. The aqueous phase can be added to the oil-surfactant mixture in a drop-wise manner slowly while the mixture is being stirred. The mixture is stirred until an emulsion is formed. The emulsion includes water-in-oil droplets that each contains DNA templates, captures, and probes. The emulsion can be placed into individual wells of a PCR plate, and PCR and hybridization reaction can be conducted. After the reactions are completed, aliquots of the emulsion can be placed on microscope slides and imaged as described above.

Real-time PCR on the same DNA template used in the emulsion can be conducted to verify the data obtained from image analysis of the emulsion. In addition, after image analysis of the emulsion is completed, the emulsion with positive signals can be broken to isolate the capture-probe-target complexes. See, Dressman et al. (2003), supra. The isolated capture-probe-target complexes can be further subjected to image analysis to confirm the results obtained from direct image analysis of the emulsion.

A skilled practitioner would appreciate that there are a number of possible configurations and designs using emulsions. In one embodiment, emulsions can be prepared in which each different colored-droplet contains a different capture-probe combination. In another embodiment, the same droplets can each contain the same capture but different probes. For example, each droplet/capture can identify a specific organism type, and different probes can be used to distinguish organism subtypes. A skilled practitioner would also know to include appropriate positive and negative controls.

Kits

Described herein are also kits for carrying out any of the above-described methods. A kit can include one or more captures and one or more probes. A kit can also contain additional components such as reagents, PCR primers, positive and negative controls, and instructions.

The specific examples below are to be construed as merely illustrative, and not limitative of the remainder of the disclosure in any way whatsoever. All publications cited herein are hereby incorporated by reference in their entirety.

Example 1

Warfarin Sensitivity Genotyping

Captures and probes were used to carry out warfarin sensitivity genotyping.

Table 1 below shows the sequences of biotin-labeled captures, Texas Red- or FAM-labeled controls, and Cy3 or Cy5-labeled allele-specific probes.

TABLE 1

| biotin-labeled capture | 5' biotin-c12-CTT TGGAGACCAGCCCATGGGGACAGAGTCAGA (SEQ ID NO: 1) |
|---|---|
| control oligonucleotide | 5'(Texas Red)- GTCCTCAATGCTCCTCTTCCC (SEQ ID NO: 2) (contains one SNP in CYP) |

TABLE 1-continued

| | |
|---|---|
| control oligonucleotide | 5' phos-GTCCTCAATGCTCCTCTTCCC-FAM (SEQ ID NO: 3) (contains one SNP in CYP) |
| Cy3-labled SNP1-A1 probe | 5' Cy3-CACATTTGGTCCATTGTCATGTGT (SEQ ID NO: 4) (VKORC1 SNP rs 7294) |
| Cy5-labeled SNP1-A2 probe | 5' Cy5-ACATTTGGTCCATTGTCATGTGC (SEQ ID NO: 5) (VKORC1 SNP rs 7294) |
| Cy3-labled SNP2-A3 probe | 5' Cy3-CGGGCTTCCTCTTGAACACG (SEQ ID NO: 6) (CYP 2C9 SNP rs 1799853) |
| Cy5-labeled SNP2-A4 probe | 5' Cy5-CGGGCTTCCTCTTGAACACA (SEQ ID NO: 7) (CYP 2C9 SNP rs 1799853) |

The biotin-labeled capture was conjugated to streptavidin-coated beads. 3.0 µl of bead-conjugated capture was added to 10.0 µl of binding buffer and incubated at room temperature for one hour. The solution was washed three times and re-suspended in 10 µl of binding buffer for use in the later hybridization step.

10 µl of blood sample was mixed with 20 µl of a lysis buffer in a tube, and then 50 µl of double distilled water was added to the tube. Next, 10 µl of lamda exonuclease (New England Biolabs) was added to the tube, which was subsequently incubated in a dry box at 37° C. for 30 minutes. The residual enzyme was inactivated by heating the tube at 95° C. for half a minute. The tube was then cooled in an ice box.

1.0 µl of bead-conjugated capture, 0.5 µl of unconjugated capture, 0.5 µl of each control, 0.5 µl of each probe (100 ng) were mixed well together in a 200 µl Eppendorf tube. 79.5 µl of the above-described lamda exonuclease-pretreated sample, 10 µl of a hybridization buffer, and 7 µl of double distilled water were added to the tube. The content in the tube was mixed well. The tube was then incubated in a temperature-controlled chamber at 65° C. for 10 minutes, followed by a decreasing temperature gradient from 65° C. to 45° C. at the rate of 1 minute per degree of temperature change. Next, the content of the tube was washed three times at 42° C. with a wash solution containing 1 mM EDTA, 1% SDS, and 10 mM NaCl. The content was then subjected to image analysis. An oligonucleotide complementary to a bovine DNA sequence was used as a negative control.

Figure 3:
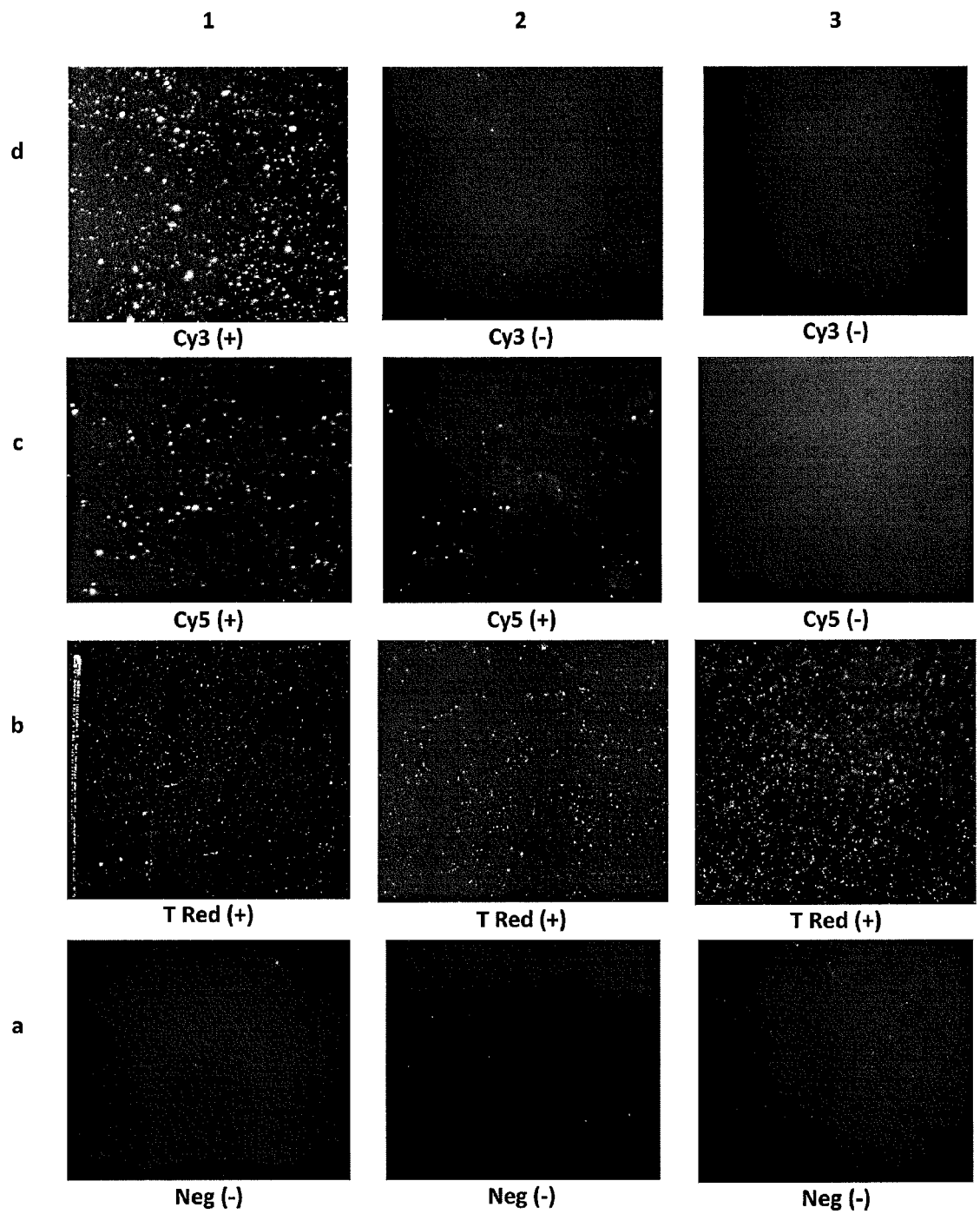
FIG. 3 is a set of images that show the results of a warfarin genotyping test in accordance with an embodiment.

The allele-specific probe sequences were designed to each contain a base complementary to the SNP nucleotide in the target gene. The capture was designed to hybridize to a sequence in the target gene that does not contain a SNP of interest. If the target gene did not contain the SNP, the probe would not bind and hence the color associated with that probe would not be observed. See, FIG. 3, panels 2d, 3d, and 3c. Conversely, if the target gene did contain the SNP, the color associated with the probe for that SNP would be observed. See, FIG. 3, panels 1d, 1c, and 2c. The Texas Red-labeled control sequence showed positive reactions. See, FIG. 3, panels 1b, 2b, and 3b. As expected, the bovine DNA negative control failed to produce any signal. See, FIG. 3, panels 1a, 2a, and 3a).

As an example, testing results from one heterozygous control, one homozygous control, and 8 clinical samples are shown in Table 2 below. The results were also verified with those obtained with another method known in the art.

TABLE 2

| SNP1 (rs. 7294) | Cy3 probe (A) | Cy5 probe (G) | Result |
|---|---|---|---|
| AD | − | + | Heterozygous |
| HD | + | + | Homozygous |
| Sample 1 | + | − | Heterozygous |
| Sample 2 | − | + | Heterozygous |
| Sample 3 | + | − | Heterozygous |
| Sample 4 | − | + | Heterozygous |
| Sample 5 | + | + | Homozygous |
| Sample 6 | − | − | Heterozygous |
| Sample 7 | + | + | Homozygous |
| Sample 8 | + | + | Homozygous |

Example 2

Emulsion PCR

The following components were thoroughly mixed in a 50 ml-centrifuge tube at 25° C. to prepare the oil-surfactant mixture:

| Components | Final concentration |
|---|---|
| Span 80 | 4.5% (vol/vol) |
| Tween 80 | 0.4% (vol/vol) |
| Triton X-100 | 0.05% (vol/vol) |
| Fluorescent dye (FAM dye) | 0.01% (vol/vol) |
| Mineral oil | to 1 ml (final volume) |

400 µl of the oil-surfactant mixture was moved to CryoTube ampoules and 3×8 mm magnetic stir bars were added. The mixture was blended with the stir bars at 1,000 rpm.

The following components were mixed to form the water phase of the emulsion, i.e., the PCR reaction buffer:

| | |
|---|---|
| 10× Clone Pfu buffers | 1 µl |
| BSA (100 g/l) | 1 µl |
| Forward primers (10 µM) | 1 µl |
| Reverse primers (10 µM) | 1 µl |
| dNTPs (5 mM) | 2 µl |
| Pfu Turbo DNA polymerase | 1 µl |
| Probe 1-cy3 (100 nm) | 0.5 µl |
| Probe 2-cy5 (100 nm) | 0.5 µl |
| Template DNA | ≤10⁹ molecules (1.66 fmol) |
| Water | to 10 µl (final volume) |

10 µl of a lysis buffer (1 µl of perfluorohexane (Fluorinert™), 8 µl of Polytetramethylene glycol and 1 µl of Triton X-100), the PCR reaction buffer, and 20 µl of a whole blood sample were mixed together. The mixture stood for about 3 minutes until its color changed to green. 20 µl of the oil-surfactant mixture was added to the mixture and mixed at room temperature for 3 minutes. An emulsion was formed in which PCR reagents and nucleic acids were encapsulated within oil. Note that the lysis buffer and the PCR buffer can be added separately or pre-mixed before addition.

Figure 4:
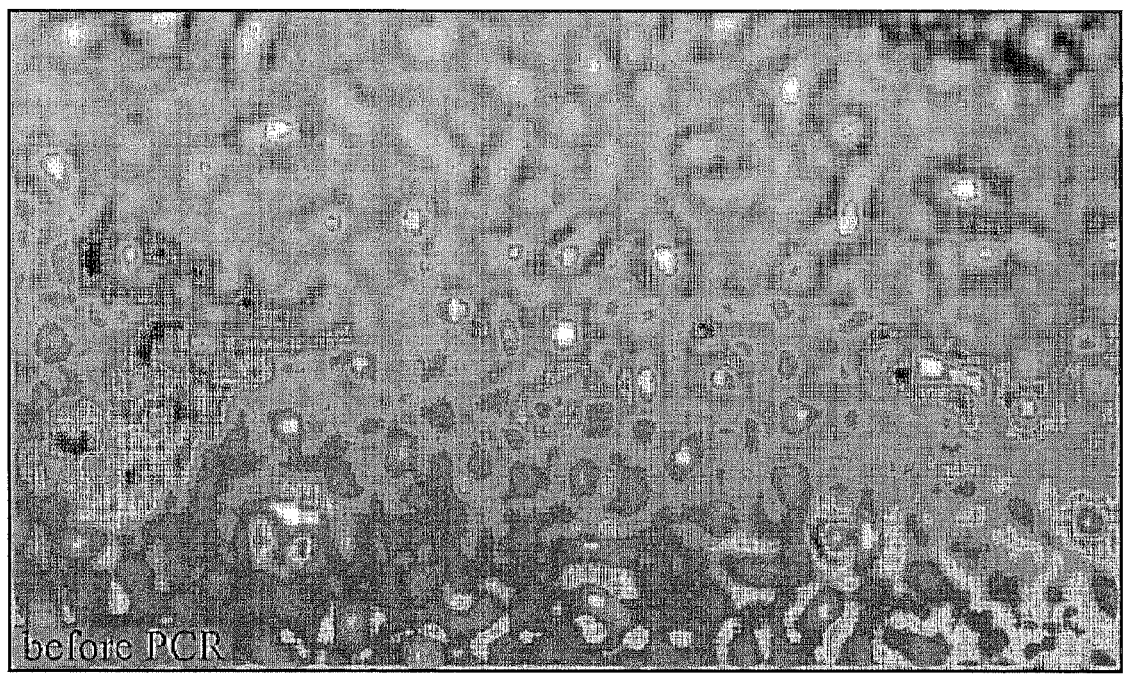
FIG. 4 is a microscopic photograph (at 50 fold magnification) showing an emulsion made from a mixture of a blood sample, a lysis buffer and a PCR reaction buffer before PCR was conducted in accordance with an embodiment. The white portions are the fluorescent dyes, and the black portions are the gel-like materials and the background.

FIG. 4 shows a microscopic photograph (at 50 fold magnification) of the emulsion before the PCR was carried out. The white portions in FIG. 4 show encapsulated fluorescent-labeled nucleic acids, while the black portions show the background and gel-like materials.

The emulsion was then subjected to PCR under the following conditions: 95° C., for 5 minutes, 94° C., for 45 seconds, 65° C., for 45 seconds, 55° C., for 45 seconds, 72° C., for 60 seconds, for 40 cycles. The emulsion was then kept at 72° C. for 5 minutes and stored at 4° C. for optical analysis.

Figure 5:
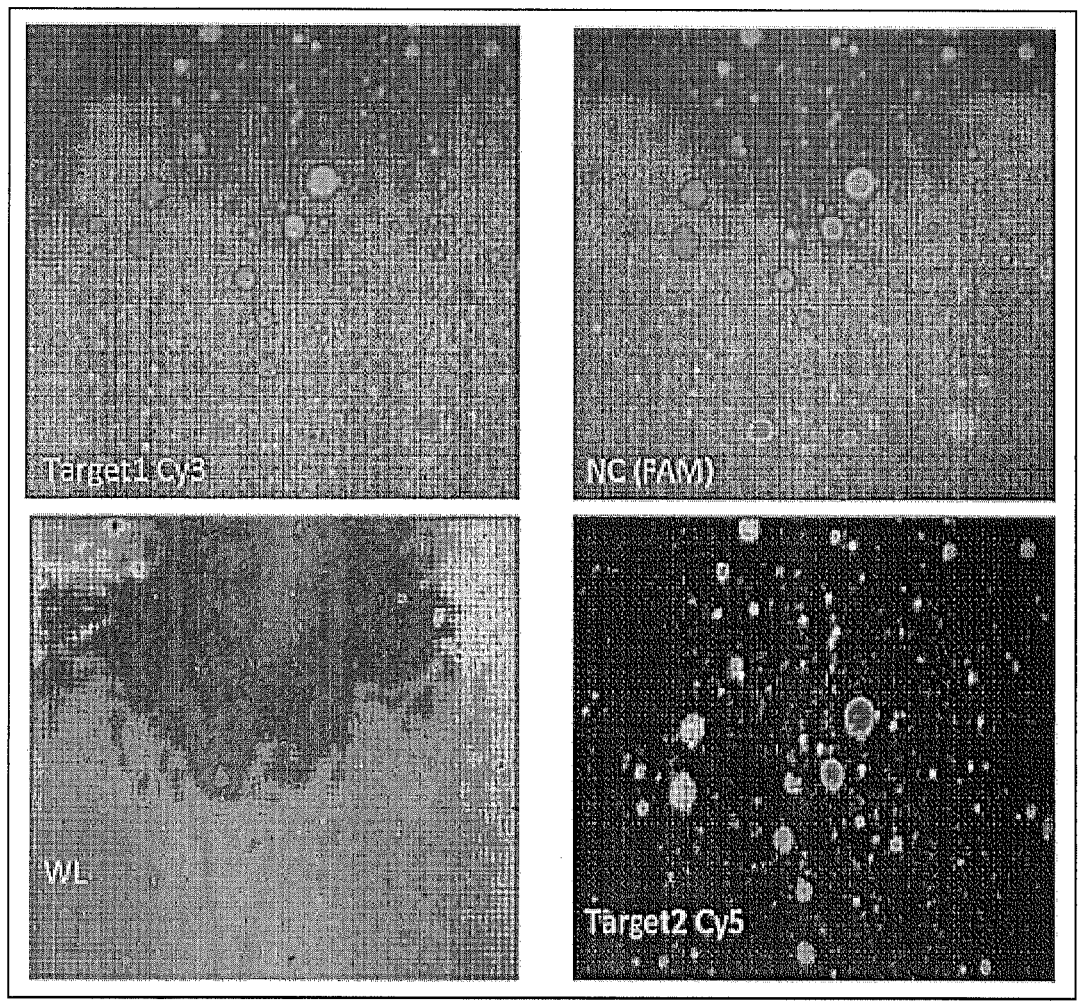
FIG. 5 is a set of microscopic photographs (at 20 fold magnification) showing an emulsion after emulsion PCR in accordance with an embodiment. The top left panel (Target1 Cy3) and the bottom right panel (Target2 Cy5) show the two labeled probes, i.e., probe 1-cy3 and probe 2-cye5, respectively. The top right panel (Negative Control (FAM)) shows the oil phase labeled with FAM dye. The left bottom panel (WL) shows the emulsion under white light.

Microscopic photographs (at 20 fold magnification) of the emulsion after the PCR are shown in FIG. 5. The top left panel (Target1 Cy3) and the bottom right panel (Target2 Cy5) show the two labeled probes, i.e., probe 1-cy3 and probe 2-cye5, respectively. The top right panel (Negative Control (FAM)) shows the oil phase labeled with FAM dye. The left bottom panel (WL) shows the emulsion under white light.

The results demonstrated that complete oil-ball shapes were formed after the emulsion was subjected to PCR, which was beneficial for the subsequent optical analysis.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

It will be apparent to those skilled in the art that various modifications and variations can be made to the disclosed embodiments. Thus, other embodiments are also within the claims.

---

What is claimed is:

1. A method of identifying one or more target nucleic acids, the method comprising:
providing a sample containing nucleic acid molecules;
mixing the sample with one or more captures and one or more probes to obtain a mixture, wherein (i) each capture is labeled with one or more detectable labels such that it is distinguishable from the other captures by its detectable labels, and contains a capture nucleic acid sequence complementary to a first target sequence in a target nucleic acid, and (ii) each probe is labeled with one or more detectable labels such that it is distinguishable from the other probes by its detectable labels, and contains a probe sequence that is complementary to a second target sequence in a target nucleic acid, whereby a combination of detectable labels identifies a target nucleic acid molecule;
allowing the one or more captures and the one or more probes to hybridize to the nucleic acid molecules, thereby complexes each containing a target nucleic acid, a capture, and a probe are formed; and
determining the detectable labels bound to the complexes by imaging the detectable labels separately to obtain individual images, whereby one or more target nucleic acids are identified;
wherein the hybridization step is carried out in an emulsion.

2. The method of claim 1, wherein the detectable labels are colored labels.

3. The method of claim 2, wherein each of the colored labels is detectable with visible light, fluorescence, luminescence, LED light, UV light, laser, or a combination thereof.

4. The method of claim 1, wherein each probe is specific for one or more SNPs or one or more mutations in a second target sequence.

5. The method of claim 4, wherein the target nucleic acids include the vitamin K epoxide reductase gene or a fragment thereof and the cytochrome p450 gene or a fragment thereof, and the SNPs include SNPs associated with warfarin sensitivity.

6. The method of claim 1, wherein each capture contains a small solid particle that is labeled with one or more detectable labels.

7. A method of identifying one or more target nucleic acids, the method comprising:
providing a sample containing nucleic acid molecules;
mixing the sample with a lysis buffer, primers for amplifying a target nucleic acid, PCR reagent, one or more captures, and one or more probes to obtain a mixture, wherein (i) each capture is labeled with one or more detectable labels such that it is distinguishable from the other captures by its detectable labels, and contains a capture nucleic acid sequence complementary to a first target sequence in a target nucleic acid, and (ii) each probe is labeled with one or more detectable labels such that it is distinguishable from the other probes by its detectable labels, and contains a probe sequence that is complementary to a second target sequence in a target nucleic acid,
conducting PCR on the mixture to amplify a target nucleic acid;
allowing the one or more captures and the one or more probes to hybridize to the nucleic acid molecules, thereby complexes each containing a target nucleic acid, a capture, and a probe are formed; and
determining the detectable labels bound to the complexes by imaging the detectable labels separately to obtain individual images, whereby one or more target nucleic acids are identified.

8. The method of claim 7, wherein the mixing step, the PCR step, and the hybridization step are conducted in the same container, whereby the complexes are formed in the container.

9. The method of claim 8, further comprising, after the hybridization step, washing the complexes in the container.

10. The method of claim 9, wherein the hybridization step, the washings step, and the determining step are conducted without an intervening step.

11. The method of claim 7, wherein the detectable labels are colored labels.

12. The method of claim 11, wherein each of the colored labels is detectable with visible light, fluorescence, luminescence, LED light, UV light, laser, or a combination thereof.

13. The method of claim 7, wherein each probe is specific for one or more SNPs or one or more mutations in a second target sequence.

14. The method of claim 13, wherein the target nucleic acids include the vitamin K epoxide reductase gene or a fragment thereof and the cytochrome p450 gene or a fragment thereof, and the SNPs include SNPs associated with warfarin sensitivity.

15. The method of claim 7, wherein each capture contains a small solid particle that is labeled with one or more detectable labels.

\* \* \* \* \*